United States Patent
Ishikawa et al.

(10) Patent No.: US 11,309,073 B2
(45) Date of Patent: Apr. 19, 2022

(54) DISPLAY CONTROL DEVICE, DISPLAY CONTROL METHOD, AND DISPLAY CONTROL PROGRAM

(71) Applicant: FUJIFILM Corporation, Tokyo (JP)

(72) Inventors: Shigetoshi Ishikawa, Kanagawa (JP); Hirona Yumbe, Kanagawa (JP); Akemi Oda, Kanagawa (JP); Yasuhisa Kaneko, Kanagawa (JP); Keiji Tsubota, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 136 days.

(21) Appl. No.: 16/402,211

(22) Filed: May 2, 2019

(65) Prior Publication Data

US 2019/0348170 A1  Nov. 14, 2019

(30) Foreign Application Priority Data

May 11, 2018 (JP) .............................. JP2018-092395
Sep. 27, 2018 (JP) .............................. JP2018-181292

(51) Int. Cl.
*G16H 30/40* (2018.01)
*A61B 1/00* (2006.01)
*G06F 9/30* (2018.01)

(52) U.S. Cl.
CPC ......... *G16H 30/40* (2018.01); *A61B 1/00048* (2013.01); *G06F 9/3004* (2013.01)

(58) Field of Classification Search
CPC ............................... A61B 5/743; G16H 15/00
See application file for complete search history.

(56) References Cited

U.S. PATENT DOCUMENTS 9,402,585 B2   8/2016 Hatano et al.
2002/0186818 A1* 12/2002 Arnaud et al.
2007/0088525 A1   4/2007 Fotiades et al.
(Continued)

FOREIGN PATENT DOCUMENTS

JP   H09101998   4/1997
JP   2009110282  5/2009
(Continued)

OTHER PUBLICATIONS

Office Action of Japan Counterpart Application, with English translation thereof, dated Jun. 1, 2021, pp. 1-5.

*Primary Examiner* — Ross Varndell
(74) *Attorney, Agent, or Firm* — JCIPRNET

(57) ABSTRACT

A display control device includes: a display control unit that displays a graph representing a history of inspection results including a last inspection result of a subject individual and a predetermined number of previous inspection results from the last inspection result for a predetermined inspection item among plural inspection items in the subject, the graph having a first axis representing the inspection results and a second axis representing a time series, and performs control for displaying information representing plural inspection results of at least one of the subject individual or the same variety as a variety of the subject individual on a position corresponding to a specific point of time of the second axis along a direction of the first axis with a different color or density according to a frequency of each inspection result.

22 Claims, 10 Drawing Sheets

(56) References Cited

U.S. PATENT DOCUMENTS

| | | | |
|---|---|---|---|
| 2012/0179071 A1* | 7/2012 | Skelton | |
| 2014/0088993 A1* | 3/2014 | Itoh et al. | |
| 2016/0004843 A1* | 1/2016 | Hoshino | |
| 2017/0143222 A1* | 5/2017 | Mann | A61B 5/316 |
| 2018/0064397 A1 | 3/2018 | Horikawa et al. | |
| 2019/0029610 A1 | 1/2019 | Utsunomiya et al. | |

FOREIGN PATENT DOCUMENTS

| | | |
|---|---|---|
| JP | 2014150845 | 8/2014 |
| JP | 2016150102 | 8/2016 |
| JP | 2016218536 | 12/2016 |
| JP | 2018005584 | 1/2018 |
| JP | 2019024943 | 2/2019 |

* cited by examiner

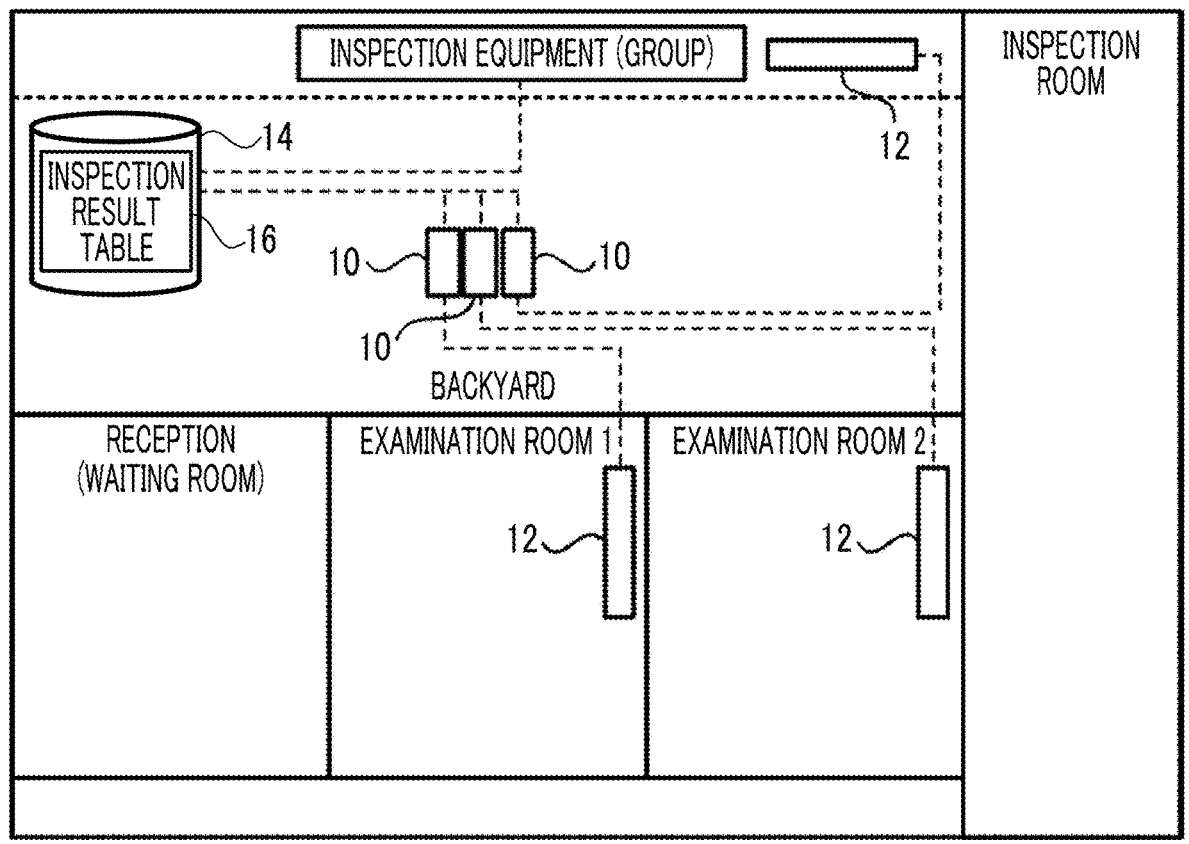

DISPLAY CONTROL DEVICE, DISPLAY CONTROL METHOD, AND DISPLAY CONTROL PROGRAM

CROSS-REFERENCE TO RELATED APPLICATIONS

This application claims priority from Japanese Patent Applications No. 2018-092395, filed on May 11, 2018, and No. 2018-181292, filed on Sep. 27, 2018, the disclosures of which are incorporated by reference herein in their entirety.

BACKGROUND

Field of the Invention

The present disclosure relates to a display control device, a display control method, and a storage medium storing a display control program.

Related Art

In the related art, the presence or absence of an abnormality is determined for each inspection item in an inspection result of a medical examination of a human, and a display order of the inspection items of the inspection result determined to be abnormal is decided (for example, JP2009-110282A).

Biological information of a human is accumulated, and the accumulated biological information is graphed (for example, JP1997-101998A (JP-H09-101998A)).

However, in the techniques described in JP2009-110282A and JP1997-101998A (JP-H09-101998A), for example, in a case where a last inspection result is an abnormal value, it is not possible to determine whether or not the inspection result is abnormal occasionally or whether or not there is a strong tendency that the inspection result is abnormal. Similarly, for example, in a case where the last inspection result is a normal value, it is not possible to determine whether or not the inspection result is normal occasionally or whether or not there is a strong tendency that the inspection result is normal. For this reason, there is a problem in that it is not possible to support appropriate diagnosis of a subject by an examiner, such as a physician.

SUMMARY

The present disclosure has been accomplished in consideration of the above circumstances, and an object of the present disclosure is to provide a display control device, a display control method, and a storage medium storing a display control program capable of supporting appropriate diagnosis of a subject by an examiner.

In order to achieve the above-described object, the present disclosure provides a display control device comprising a display control unit that displays a graph representing a history of inspection results including a last inspection result of a subject individual and a predetermined number of previous inspection results from the last inspection result for a predetermined inspection item among a plurality of inspection items in the subject, the graph having a first axis representing the inspection results and a second axis representing a time series, and performs control for displaying information representing a plurality of inspection results of at least one of the subject individual or the same variety as a variety of the subject individual on a position corresponding to a specific point of time of the second axis along a direction of the first axis with a different color or density according to a frequency of each inspection result.

In the display control device of the present disclosure, in a case where the subject is an animal, the variety may be an animal variety, and in a case where the subject is a human, the variety may be a human race.

In the display control device of the present disclosure, in a case of performing control for displaying information representing the plurality of inspection results of the subject individual, the display control unit may perform control for displaying information representing a plurality of previous inspection results before the predetermined number of inspection results of the subject individual.

In the display control device of the present disclosure, in a case of performing control for displaying information representing the plurality of inspection results of the same variety as the variety of the subject individual, the display control unit may perform control for displaying information representing all inspection results to be acquired from a storage device storing the inspection results of the same variety or a part of last inspection results among all the inspection results.

In the display control device of the present disclosure, the display control unit may perform control for displaying information representing the plurality of inspection results of both of the subject individual and the same variety as the variety of the subject individual.

In the display control device of the present disclosure, information representing the plurality of inspection results may be a scatter plot on one axis in which a point corresponding to each of the plurality of inspection results is plotted on the position corresponding to the specific point of time.

In the display control device of the present disclosure, in a case where a plurality of inspection results having the same value are present, the display control unit may perform control for displaying each piece of information representing the inspection results having the same value on a position corresponding to a different point of time along the direction of the first axis.

In the display control device of the present disclosure, the display control unit may perform control for displaying information representing the plurality of inspection results by a histogram.

In the display control device of the present disclosure, the display control unit may perform the control by weighting a frequency of an inspection result using a smaller weight value when the inspection result is older.

In the display control device of the present disclosure, the display control unit may perform control for displaying information representing the plurality of inspection results by changing a display state depending on at least one of the number of the plurality of inspection results or a proportion of inspection results before a predetermined point of time in the plurality of inspection results.

In the display control device of the present disclosure, the display control unit may perform control for displaying information representing the plurality of inspection results by changing color depending on at least one of the number of the plurality of inspection results or the proportion of the inspection results before the predetermined point of time in the plurality of inspection results.

The display control device of the present disclosure may further comprise a determination unit that determines whether or not an inspection result is an abnormal value for each inspection item, and the predetermined inspection item may be an inspection item for which an inspection result is determined to be an abnormal value by the determination unit.

In the display control device of the present disclosure, the display control unit may perform control for displaying the graph preferentially for the inspection item, for which the inspection result is determined to be the abnormal value, when a degree of abnormality is higher.

In the display control device of the present disclosure, the display control unit may further perform control for displaying a plurality of inspection items by changing color between an inspection item, for which an inspection result is an abnormal value, and an inspection item, for which an inspection result is a normal value.

In the display control device of the present disclosure, the display control unit may perform control for displaying the inspection item, for which the inspection result is the abnormal value, by further changing color depending on whether the inspection result is less than a lower limit value of the normal value or exceeds an upper limit value of the normal value.

In the display control device of the present disclosure, the display control unit may perform control for displaying an inspection item, for which an inspection result is less than the lower limit value of the normal value, by changing density of color depending on a degree of difference from the lower limit value, and may perform control for displaying an inspection item, for which an inspection result exceeds the upper limit value of the normal value, by changing density of color depending on a degree of difference from the upper limit value.

In the display control device of the present disclosure, the display control unit may perform control for arranging and displaying the plurality of inspection items in tiles.

In the display control device of the present disclosure, the display control unit may perform control for switching between a first display screen, on which the graph is displayed in a medical examination of the subject, and a second display screen, on which the graph is displayed in a temporary inspection including inspection items different from inspection items in the medical examination.

In the display control device of the present disclosure, the number of previous inspection results to be displayed as the graph on the first display screen may be greater than the number of previous inspection results to be displayed as the graph on the second display screen.

In the display control device of the present disclosure, the display control unit may perform control for displaying the graph including inspection results of the medical examination as the history of the inspection results for the inspection items included in the medical examination among the inspection items in the temporary inspection.

In order to achieve the above-described object, the present disclosure provides a display control method executes by a computer, the method including: displaying a graph representing a history of inspection results including a last inspection result of a subject individual and a predetermined number of previous inspection results from the last inspection result for a predetermined inspection item among a plurality of inspection items in the subject, the graph having a first axis representing the inspection results and a second axis representing a time series, and performing control for displaying information representing a plurality of inspection results of at least one of the subject individual or the same variety as a variety of the subject individual on a position corresponding to a specific point of time of the second axis along a direction of the first axis with a different color or density according to a frequency of each inspection result.

In order to achieve the above-described object, the present disclosure provides a non-transitory storage medium storing a program that causes a computer to execute a display control processing, the display control processing including: displaying a graph representing a history of inspection results including a last inspection result of a subject individual and a predetermined number of previous inspection results from the last inspection result for a predetermined inspection item among a plurality of inspection items in the subject, the graph having a first axis representing the inspection results and a second axis representing a time series, and performing control for displaying information representing a plurality of inspection results of at least one of the subject individual or the same variety as a variety of the subject individual on a position corresponding to a specific point of time of the second axis along a direction of the first axis with a different color or density according to a frequency of each inspection result.

In order to achieve the above-described object, the present disclosure provides a display control device comprising a display control unit that displays a graph representing a history of inspection results including a last inspection result of a subject individual and a predetermined number of previous inspection results from the last inspection result for a predetermined inspection item among a plurality of inspection items in the subject, the graph having a first axis representing the inspection results and a second axis representing a time series, and performs control for displaying information representing a plurality of inspection results of at least one of the subject individual or the same variety as a variety of the subject individual on a position corresponding to a specific point of time of the second axis along a direction of the first axis by a histogram of the same color and density.

In order to achieve the above-described object, the present disclosure provides a display control method executed by a computer, the method including: displaying a graph representing a history of inspection results including a last inspection result of a subject individual and a predetermined number of previous inspection results from the last inspection result for a predetermined inspection item among a plurality of inspection items in the subject, the graph having a first axis representing the inspection results and a second axis representing a time series, and performing control for displaying information representing a plurality of inspection results of at least one of the subject individual or the same variety as a variety of the subject individual on a position corresponding to a specific point of time of the second axis along a direction of the first axis by a histogram of the same color and density.

In order to achieve the above-described object, the present disclosure provides a non-transitory storage medium storing a program that caused a computer to execute a display control processing, the display control processing including; displaying a graph representing a history of inspection results including a last inspection result of a subject individual and a predetermined number of previous inspection results from the last inspection result for a predetermined inspection item among a plurality of inspection items in the subject, the graph having a first axis representing the inspection results and a second axis representing a time series, and performing control for displaying information representing a plurality of inspection results of at least one of the subject individual or the same variety as a variety of the subject individual on a position corresponding to a specific point of time of the second axis along a direction of the first axis by a histogram of the same color and density.

According to the present disclosure, it is possible to support appropriate diagnosis of a subject by an examiner.

BRIEF DESCRIPTION OF THE DRAWINGS

FIG. 1 is a plan view showing an example of an arrangement location of a display control device according to an embodiment.

FIG. 2 is a diagram showing an example of an inspection result table according to the embodiment.

FIG. 5 is a diagram showing an example of a first display screen according to the embodiment.

FIG. 6 is a diagram showing an example of a second display screen according to the embodiment.

FIG. 7 is a diagram showing an example of a second display screen according to a modification example.

DETAILED DESCRIPTION

Figure 3:
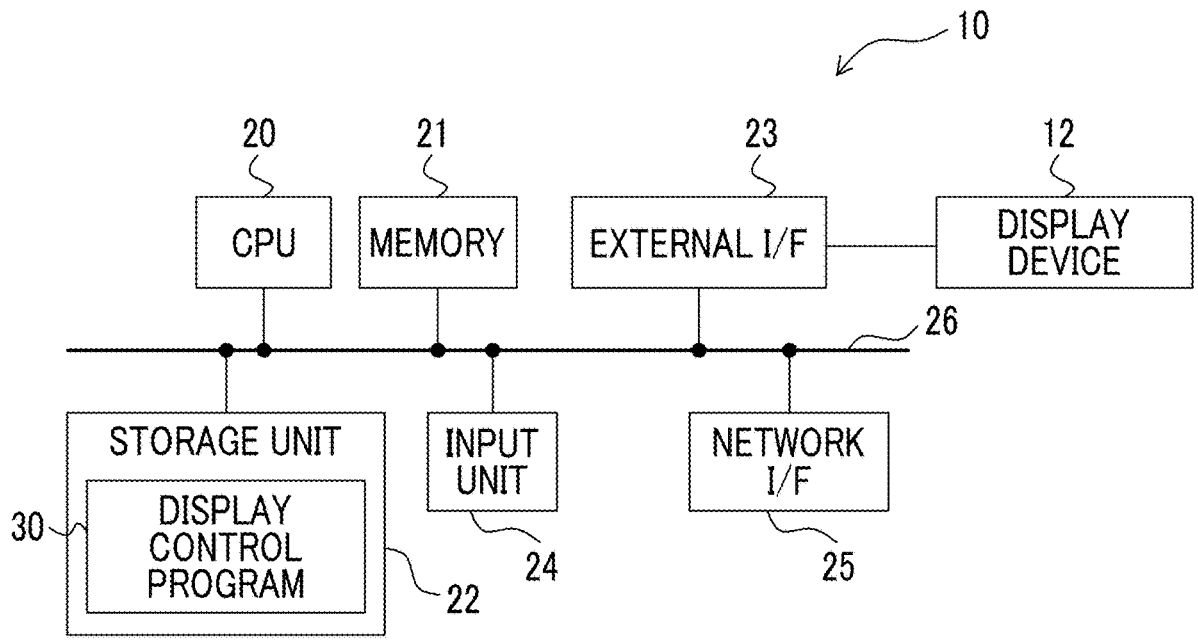
FIG. 3 is a block diagram showing an example of the hardware configuration of the display control device according to the embodiment.

Hereinafter, an embodiment for carrying out the technique of the present disclosure will be described in detail referring to the accompanying drawings.

First, an arrangement location of display control devices 10 according to the embodiment will be described referring to FIG. 1. As shown in FIG. 1, the display control devices 10 are provided in a backyard to correspond to examination rooms of an animal hospital and display devices 12 provided in the backyard. Each display device 12 is connected to the corresponding display control device 10, and the display of the display device 12 is controlled by the display control device 10. As an example of each display control device 10, a personal computer is exemplified, and as an example of each display device 12, a liquid crystal display is exemplified. The display devices 12 are provided in the examination room for explanation to an owner of a subject animal and in the backyard for pre-confirmation of an inspection result.

A storage device 14 that stores an inspection result table 16 is provided in the backyard. Each display control device 10 and the storage device 14 are connected to perform communication with each other. The storage device 14 may be, for example, a cloud server that performs communication through a network, such as the Internet. Inspection result data obtained through an inspection with inspection equipment is transferred from the inspection equipment to the storage device 14 through the network. As an example of the inspection equipment, a biochemical inspection machine that inspects protein, oxygen, nitrogen, electrolyte, and the like is exemplified in a case of blood inspection. As an example of the inspection equipment, an immunological inspection machine that inspects immunity or the like, a hemocyte counter that inspects hemocytes, or the like is exemplified. In an inspection room, inspections may be performed by an X-ray image diagnostic apparatus, an ultrasound diagnostic apparatus, an endoscope, and the like, and information of images and the like may be transferred from these apparatuses to the storage device 14 through the network.

FIG. 2 shows an example of the inspection result table 16. As shown in FIG. 2, in the inspection result table 16, an identifier (ID) as an example of identification information, a name, a sex, an age, a race, a variety, and inspection result information are stored for each subject animal. In the inspection result information, an execution date of an inspection, information representing whether or not an inspection is a medical examination (in FIG. 2, denoted as "medical examination"), and an inspection result of each inspection item obtained through an inspection with the inspection equipment are stored. In the example of FIG. 2, an inspection result where a medical examination column is "Y" represents an inspection result corresponding to an inspection item in a medical examination, and an inspection result where a medical examination column is "N" represents an inspection result corresponding to a temporary inspection including inspection items different from the inspection items in the medical examination.

The temporary inspection used herein means an inspection different from a medical examination to be performed regularly, and for example, an inspection that is performed for diagnosis of a specific disease as a result of an examination of an examiner, such as a veterinarian, is exemplified. The inspection items in the temporary inspection may include the inspection items in the medical examination. In the example of FIG. 2, though not shown, in the inspection result table 16, information representing whether or not the examiner focuses on each inspection item is also stored corresponding to each inspection item.

Next, the hardware configuration of the display control device 10 according to the embodiment will be described referring to FIG. 3. As shown in FIG. 3, the display control device 10 includes a central processing unit (CPU) 20, a memory 21 as a temporary storage area, and a nonvolatile storage unit 22. The display control device 10 includes an external interface (I/F) 23 to which the display device 12 is connected, an input unit 24, such as a keyboard and a mouse, and a network I/F 25 that is connected to the network. The CPU 20, the memory 21, the storage unit 22, the external I/F 23, the input unit 24, and the network I/F 25 are connected to a bus 26. The display device 12 has a display unit integrated with a touch panel, and an input of a user on the display device 12 is input to the display control device 10 through the external I/F 23.

The storage unit 22 is implemented by a hard disk drive (HDD), a solid state drive (SSD), a flash memory, or the like. In the storage unit 22 as a storage medium, a display control program 30 is stored. The CPU 20 reads the display control program 30 from the storage unit 22, then, develops the display control program 30 to the memory 21, and executes the developed display control program 30.

Figure 4:
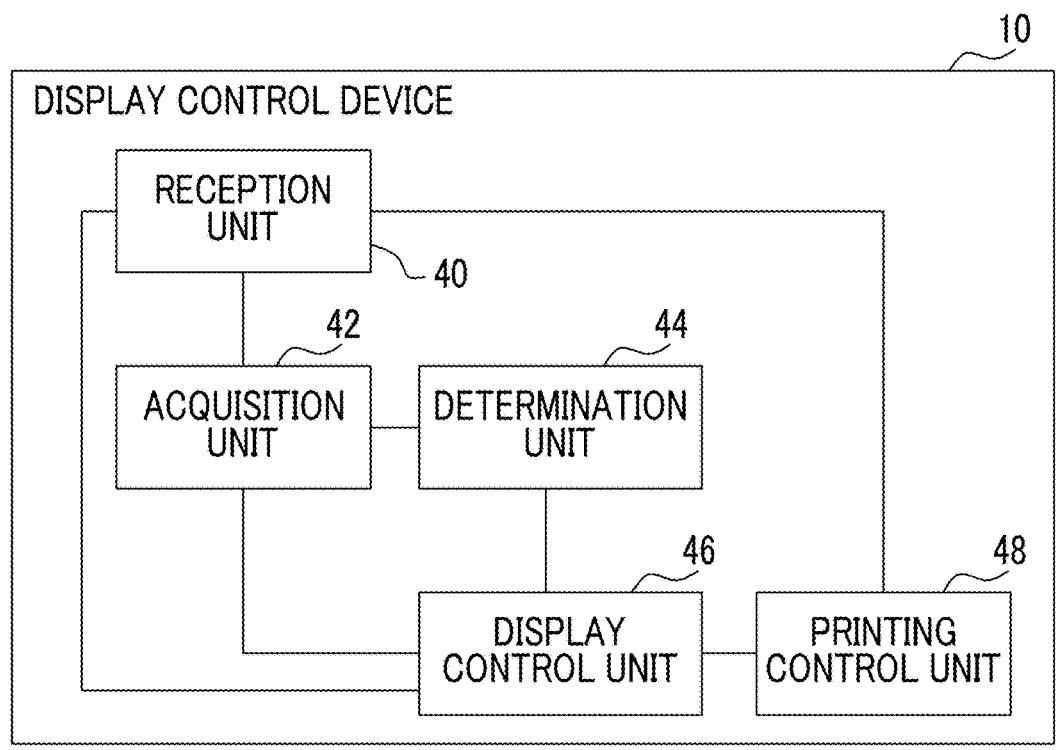
FIG. 4 is a block diagram showing an example of the functional configuration of the display control device according to the embodiment.

Next, the functional configuration of the display control device 10 according to the embodiment will be described referring to FIG. 4. As shown in FIG. 4, the display control device 10 includes a reception unit 40, an acquisition unit 42, a determination unit 44, a display control unit 46, and a printing control unit 48. The CPU 20 executes the display control program 30, thereby functioning as the reception unit 40, the acquisition unit 42, the determination unit 44, the display control unit 46, and the printing control unit 48.

The reception unit 40 receives a display instruction of a first display screen on which the inspection result of the medical examination input by the examiner is displayed. The reception unit 40 receives a display instruction of a second display screen on which the inspection result of the temporary inspection input by the examiner is displayed. In the display instructions, an ID of an animal for which an inspection result is to be displayed is included. The reception unit 40 receives a printing instruction input by the examiner. The reception unit 40 receives an inspection item input by the examiner on which the examiner focuses.

The acquisition unit 42 refers to the inspection result table 16 and acquires the name, the sex, the age, the race, the variety, and the inspection result information corresponding to the ID received by the reception unit 40.

The determination unit 44 determines whether or not the inspection result is an abnormal value for each inspection item included in the inspection result information acquired by the acquisition unit 42. Specifically, the determination unit 44 determines that the inspection result is a normal value in a case where the inspection result is equal to or greater than a lower limit value of the normal value and equal to or less than an upper limit value of the normal value determined in advance for each animal race and each inspection item. The determination unit 44 determines that the inspection result is an abnormal value in a case where the inspection result is less than the lower limit value of the normal value or exceeds the upper limit value of the normal value. In the following description, a range of equal to or greater than the lower limit value of the normal value and equal to or less than the upper limit value of the normal value is referred to as a "normal value range", and a range of less than the lower limit value of the normal value and a range exceeding the upper limit value of the normal value are referred to as an "abnormal value range". The lower limit value and the upper limit value of the normal value may be determined in advance for each animal variety and each inspection item.

The display control unit 46 performs control for switching between the first display screen and the second display screen in response to the display instruction received by the reception unit 40. The display control unit 46 performs control for displaying, on the display device 12, a graph representing a history of the inspection results for an inspection item, for which an inspection result is determined to be an abnormal value by the determination unit 44, on the first display screen and the second display screen. The history of the inspection results includes a last inspection result and a predetermined number of previous inspection results from the last inspection result. The graph has a first axis representing the inspection result and a second axis representing a time series. In the embodiment, the display control unit 46 performs control for displaying the graph on the display device 12 for an inspection item, for which at least one of the last inspection result or the second last inspection result is determined to be an abnormal value. The graph of the inspection item, for which at least one of the last inspection result or the second last inspection result is an abnormal value, is displayed, whereby it is possible to make the examiner easily recognize three states of a state in which the inspection result of the inspection item is from an abnormal condition to a normal condition, a state in which the inspection result of the inspection item is from a normal condition to an abnormal condition, and a state in which an abnormal condition is continued. The display control unit 46 performs control for displaying the normal value range and the abnormal value range to be visually recognizable in the graph. The display control unit 46 may perform control for displaying any one of the normal value range and the abnormal value range to be visually recognizable in the graph.

The display control unit 46 sets the number of previous inspection results displayed as a graph on the first display screen to be greater than the number of previous inspection results displayed as a graph on the second display screen. The display control unit 46 performs control for displaying, on the display device 12, information representing a plurality of previous inspection results more than the predetermined number of inspection results on a position (in the embodiment, a position of a right end) corresponding to a specific point of time of the second axis of the graph along a direction of the first axis. At this time, the display control unit 46 performs control for displaying information representing the plurality of inspection results with different densities according to the frequency of each inspection result. The display control unit 46 may perform control for displaying information representing the plurality of inspection results with different colors according to the frequency of each inspection result. In the embodiment, the display control unit 46 performs control for displaying, on the display device 12, a scatter plot on one axis obtained by plotting rectangular points corresponding to the inspection results at a plurality of previous points of time on the position corresponding to the specific point of time of the second axis of the graph. That is, when the inspection result has a higher frequency, the points are plotted in an overlapping manner, and the density becomes higher.

The display control unit 46 performs control for displaying, on the display device 12, a graph including the inspection result of the medical examination as a history of the inspection results for the inspection items included in the medical examination among the inspection items in the temporary inspection on the second display screen.

The display control unit 46 performs control for displaying the graph on the display device 12 for the inspection item received by the reception unit 40, on which the examiner focuses, among the inspection items, for which the inspection result is determined to be a normal value by the determination unit 44.

The display control unit 46 performs control for displaying a list of last inspection results separately from the graph on each display screen. At the time of the control, the display control unit 46 performs control for displaying the normal value range and the abnormal value range to be visually recognizable.

In a case where the printing instruction is received by the reception unit 40, the printing control unit 48 performs control such that a printing apparatus (not shown) lays out and prints a screen to be displayed on the display device 12 to fit onto one sheet. It is desirable that printing is performed in color. In a case where a printed display result is viewed later, an inspection item having an abnormal value may be described in a sentence to be easily found (for example, "a blood glucose level and aspartate transaminase (AST)/glutamic oxaloacetic transaminase (GOT) exceed upper limits" or the like). Alternatively, an inspection item for which an inspection result is an abnormal value may be highlighted by changing a font to a boldfaced type, underlining letters, or changing the font to another font (for example, from Gothic to italics, or the like). Even in a case where the printing apparatus is a black-white machine, an inspection item for which an inspection result is an abnormal value may be highlighted by changing a font to a boldfaced type such that the inspection item for which the inspection result is an abnormal value is easily discriminated. In this case, an inspection item for which an inspection result is an abnormal value may be highlighted by underlining letters, changing a font to another font, increasing a font size to be greater than an inspection item for which an inspection result is a normal value, filling in color with white letters (for example, letters are white and the periphery is black), or the like.

Figure 5:
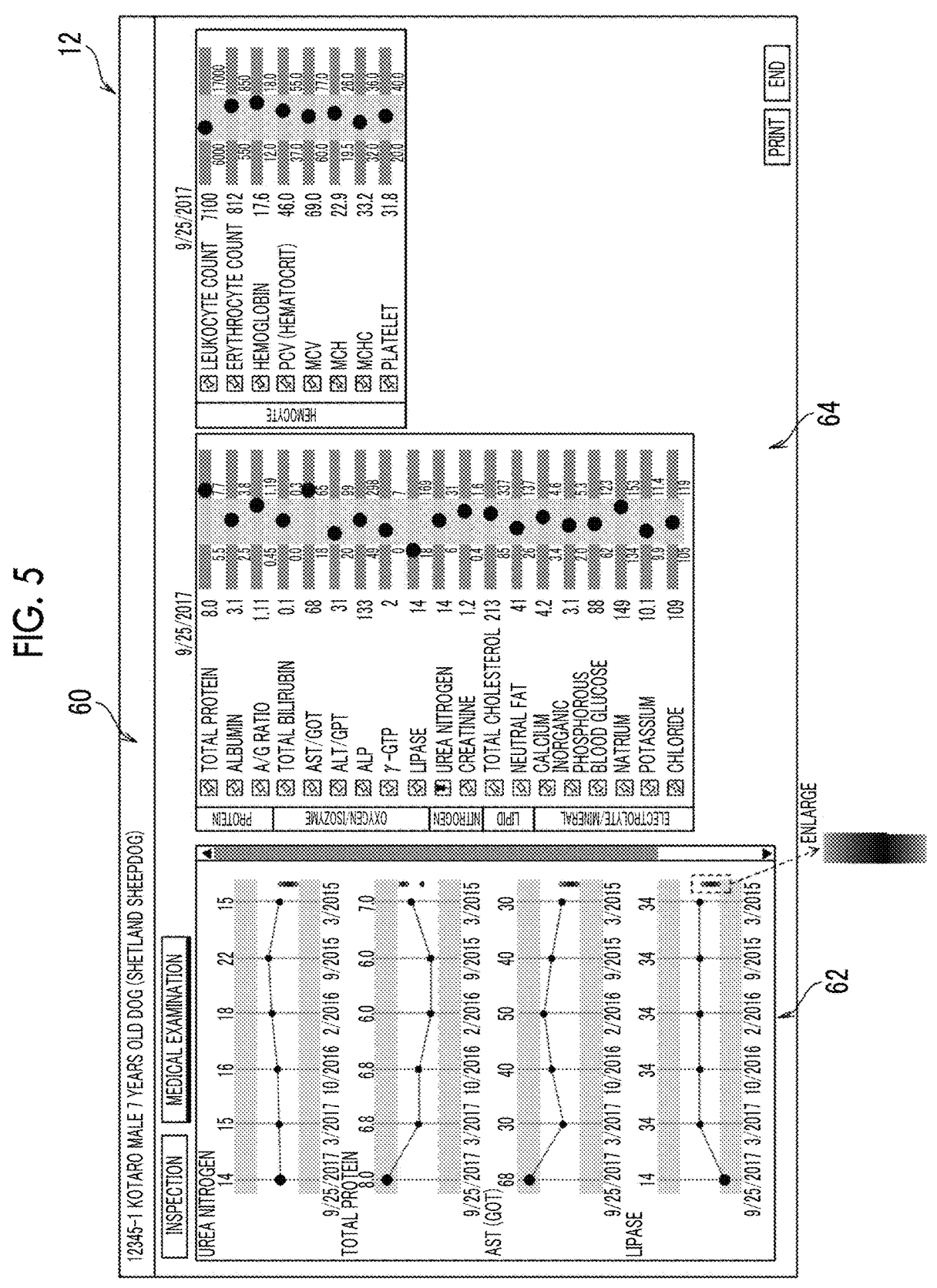

FIG. 5 shows an example of a first display screen. As shown in FIG. 5, the first display screen according to the embodiment includes display areas 60, 62, and 64. The display area 60 is a header portion, and the ID, the name, the sex, the age, the race, and the variety of the subject animal are displayed in the display area 60.

The graph is displayed in the display area 62. The vertical axis of the graph of each inspection item is the first axis representing the inspection result, and the horizontal axis is the second axis representing the time series. For example, in regard to a background color the display area 62 of the graph, the normal value range is made white and the abnormal value range is made gray, whereby the normal value range and the abnormal value range can be visually recognized. The number of histories of the inspection results of each graph on the first display screen is six in total. In regards to the colors of the points plotted in the graph, a point corresponding to the abnormal value less than the lower limit value of the normal value is made blue, a point corresponding to the abnormal value exceeding the upper limit value of the normal value is made red, and a point corresponding to the normal value is made black.

In the display area 62, information representing a plurality of previous inspection results before the inspection result displayed as the graph is displayed at a position of a right end portion of the horizontal axis along the vertical axis separately from the graph. In the embodiment, as shown in an enlarged portion of FIG. 5, in regards to all previous inspection results before the inspection result displayed as the graph, a bar is displayed such that the density is higher when the frequency of each inspection result is higher. That is, the examiner can discriminate whether an abnormal value continues, an abnormal value is generated singly, or the like from a predetermined number of last inspection results by viewing the graph. The examiner can further confirm an upper limit value, a lower limit value, and a highly frequent value of the previous inspection results by confirming the bar.

In the display area 64, a list of last inspection results is displayed. As shown in FIG. 5, the list of inspection results includes a value of the inspection result, a bar for plotting the inspection result, and a circle representing the inspection result for each inspection item. In the bar for plotting the inspection result, for example, the normal value range is shaded in white, such that the normal value range and the abnormal value range are displayed to be visually recognizable. In the display area 64, an icon representing whether or not each inspection item is pinned is displayed. The examiner can display the graph in the display area 62 by pinning a focused inspection item. In the example of FIG. 5, a state in which "urea nitrogen" is pinned is shown. In the embodiment, a graph corresponding to a pinned inspection item is displayed preferentially (in the embodiment, at an upper position) over a graph corresponding to an inspection item for which an inspection result is an abnormal value. In the display area 64, a print button and an end button are displayed.

In an upper portion of the display area 62, an inspection button and a medical examination button are displayed, and in a state in which the first display screen is displayed, the examiner designates the inspection button, such that the first display screen can be switched to the second display screen. Similarly, in a state in which the second display screen described below is displayed, the examiner designates the medical examination button, such that the second display screen can be switched to the first display screen.

Figure 6:
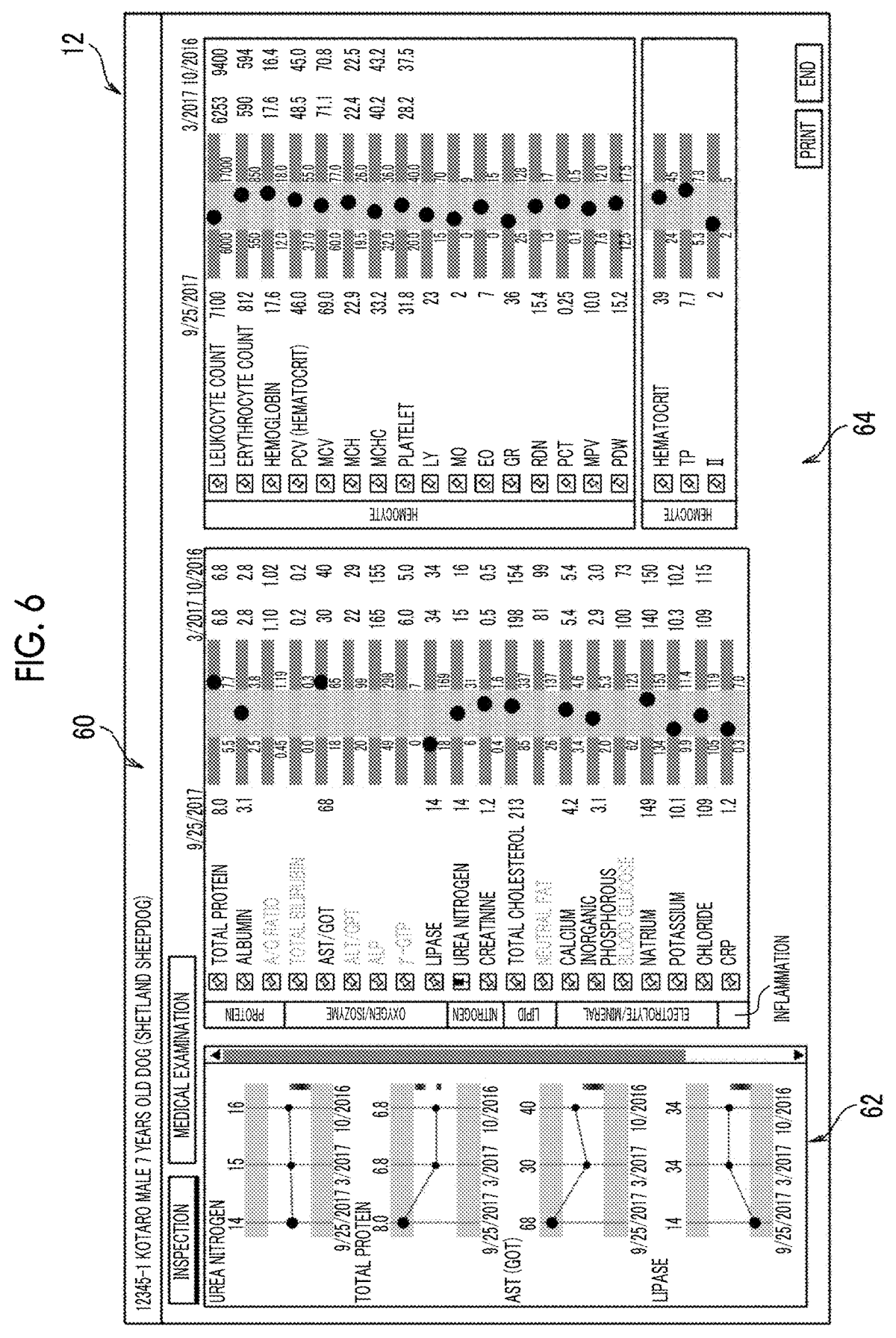

FIG. 6 shows an example of a second display screen. As shown in FIG. 6, similarly to the first display screen, the second display screen according to the embodiment includes display areas 60, 62, and 64. Hereinafter, only portions on the second display screen different from the first display screen will be described.

As shown in FIG. 6, on the second display screen, the number of inspection results displayed as the history in the graph of the display area 62 is smaller than that on the first display screen. On the second display screen, for each of the inspection items included in the medical examination among the inspection items in a last temporary inspection, the inspection result of the medical examination is included as the history of the inspection results in the graph of the display area 62.

On the second display screen, for each of the inspection items included in the medical examination among the inspection items in the last temporary inspection, the inspection result of the medical examination is displayed as the history of the inspection results in the list of inspection results of the display area 64. In the list of inspection results of the display area 64 on the second display screen, for each of the inspection items that are not included in the last temporary inspection and are included in a previous medical examination, the inspection result of the last temporary inspection is not displayed.

Figure 7:
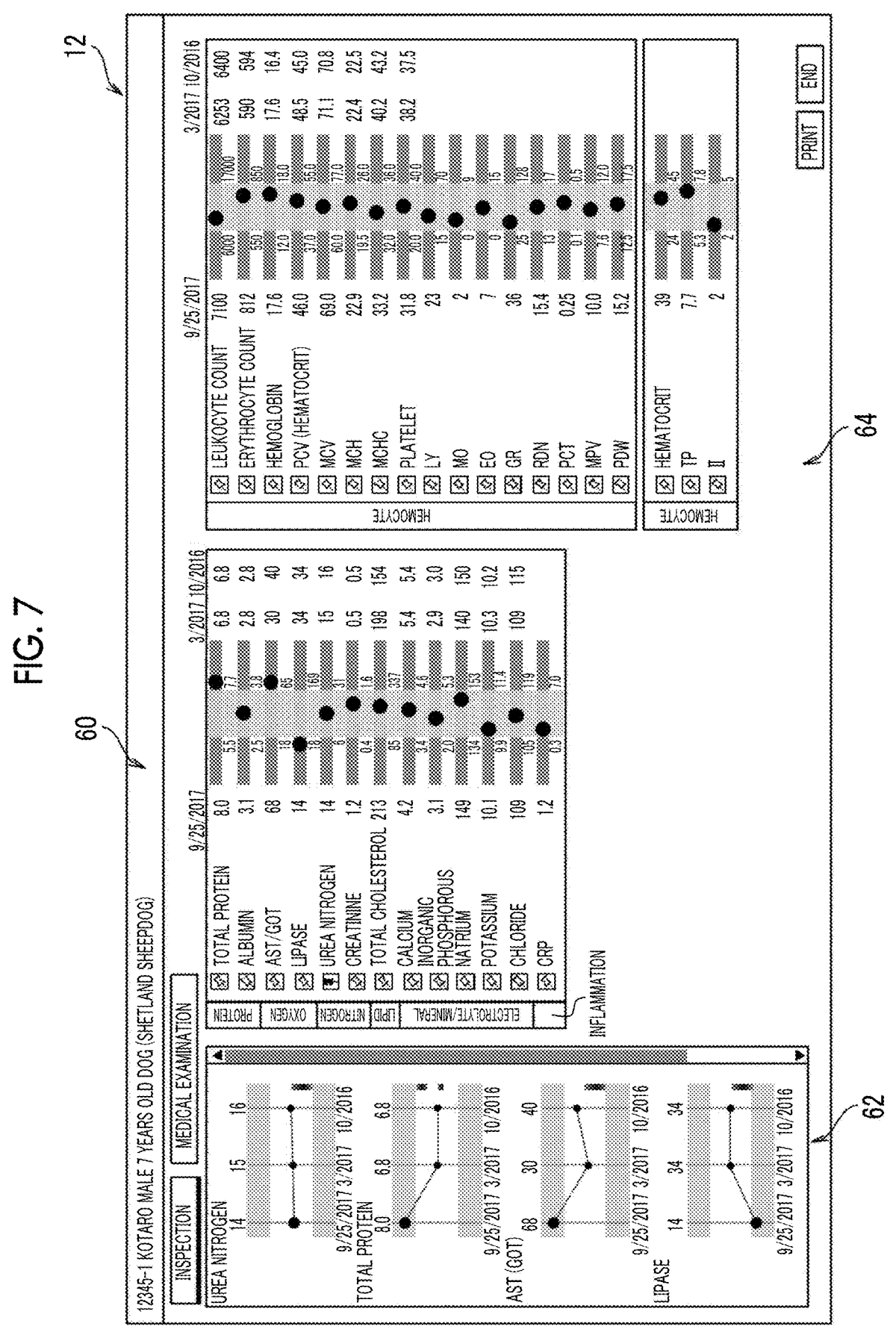

As an example, as shown in FIG. 7, in the list of inspection results of the display area 64 on the second display screen, for each of the inspection items (for example, albumin/globulin (A/G) ratio, total bilirubin, and the like shown in FIG. 6) that are not included in the last temporary inspection and are included in the previous medical examination, the inspection item itself may not be displayed.

Figure 8:
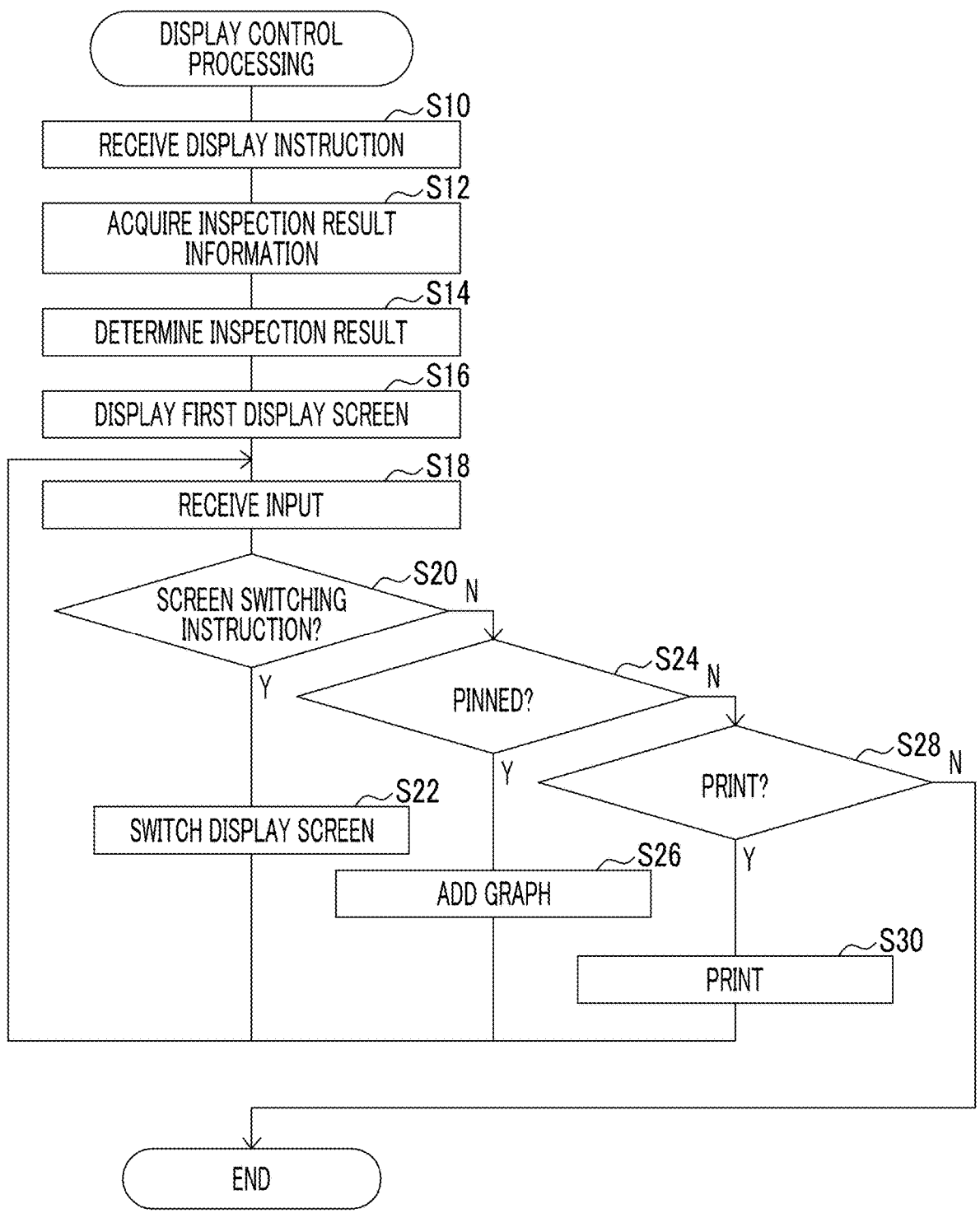
FIG. 8 is a flowchart showing an example of display control processing according to the embodiment.

Next, operation of the display control device 10 according to the embodiment will be described referring to FIG. 8. The CPU 20 executes the display control program 30, whereby display control processing shown in FIG. 8 is executed. The display control processing shown in FIG. 8 is executed, for example, in a case where the display control device 10 receives a display instruction of a screen including an ID of a subject animal input by the examiner.

In Step S10 of FIG. 8, the reception unit 40 receives the display instruction of the screen including the ID of the subject animal input by the examiner. In Step S12, the acquisition unit 42 refers to the inspection result table 16 and acquires the name, the sex, the age, the race, the variety, and the inspection result information corresponding to the ID received through the processing of Step S10.

In Step S14, as described above, the determination unit 44 determines whether or not the inspection result is an abnormal value for each inspection item included in the inspection result information acquired through the processing of Step S12. In Step S16, as described above, the display control unit 46 performs control for displaying the first display screen on the display device 12 based on various kinds of information acquired through the processing of Step S12 and a determination result through the processing of Step S14. In this way, in the embodiment, although the first display screen is displayed on the display device 12 as an initial screen, the second display screen may be displayed as an initial screen. The examiner may select which of the first display screen and the second display screen is displayed as an initial screen.

In Step S18, the reception unit 40 receives an input of the examiner. In Step S20, the display control unit 46 determines whether or not the input received through the processing of Step S18 is a switching instruction between the first display screen and the second display screen. In a case where the determination is negative, the process progresses to Step S24, and in a case where the determination is affirmative, the process progresses to Step S22. Specifically, when the inspection button is designated in a state in which the first display screen is displayed or when the medical examination button is designated in a state in which the second display screen is displayed, the determination of Step S20 is affirmative.

In Step S22, the display control unit 46 performs control for switching between the first display screen and the second display screen according to the input received through the processing of Step S18. Specifically, in a case where the inspection button is designated in a state in which the first display screen is displayed, the display control unit 46 performs control for displaying the second display screen on the display device 12. In a case where the medical examination button is designated in a state in which the second display screen is displayed, the display control unit 46 performs control for displaying the first display screen on the display device 12. When the processing of Step S22 ends, the process returns to Step S18.

In Step S24, the display control unit 46 determines whether or not the input received through the processing of Step S18 is an input corresponding to a pinning operation. In a case where the determination is negative, the process progresses to Step S28, and in a case where the determination is affirmative, the process progresses to Step S26.

In Step S26, as described above, the display control unit 46 performs control for additionally displaying the graph corresponding to the inspection result of the pinned inspection item in the display area 62. The display control unit 46 stores information representing that the examiner focuses on the pinned inspection item corresponding to the pinned inspection item in the inspection result information of the inspection result table 16. When the processing of Step S26 ends, the process returns to Step S18.

In Step S28, the display control unit 46 determines whether or not the input received through the processing of Step S18 is an input corresponding to designation of the print button. In a case where the determination is affirmative, the process progresses to Step S30. In Step S30, the printing control unit 48 performs control such that the printing apparatus lays out and prints the screen displayed on the display device 12 to fit onto one sheet. When the processing of Step S30 ends, the process returns to Step S18.

In a case where the determination of Step S28 is negative, the display control processing ends.

As described above, according to the embodiment, for the inspection item for which the inspection result is determined to be an abnormal value, the graph representing the history of the inspection results including the last inspection result and the predetermined number of previous inspection results from the last inspection result is displayed on the display device 12. In addition, information representing a plurality of previous inspection results before the predetermined number of inspection results used for the display of the graph is displayed along the direction of the first axis representing the inspection result in the graph separately from the graph. Accordingly, the examiner can visually recognize the last inspection result and the previous inspection results at one time, and as a result, it is possible to support appropriate diagnosis of an animal by the examiner.

In the embodiment, a form may be made in which, in a case where a plurality of inspection items for which the inspection result is an abnormal value are present, the graph is displayed preferentially (for example, at the upper position) in the display area 62 when the degree of abnormality is higher. In this case, a form in which the degree of abnormality is the ratio of an absolute value of the difference between the inspection result and the lower limit value to the lower limit value in a case where the inspection result is less than the lower limit value of the normal value, and is the ratio of an absolute value of the difference between the inspection result and the upper limit value to the upper limit value in a case where the inspection result exceeds the upper limit value of the normal value is exemplified. In this case, a form in which the degree of abnormality is higher when the ratio is greater is exemplified. The degree of abnormality may be derived by an artificial intelligence (AI) technique. As the AI in this case, a form in which a deep neural network with a history of inspection results for an inspection item, for which the inspection result is an abnormal value, as input and the degree of abnormality as output is applied is exemplified.

Figure 9:
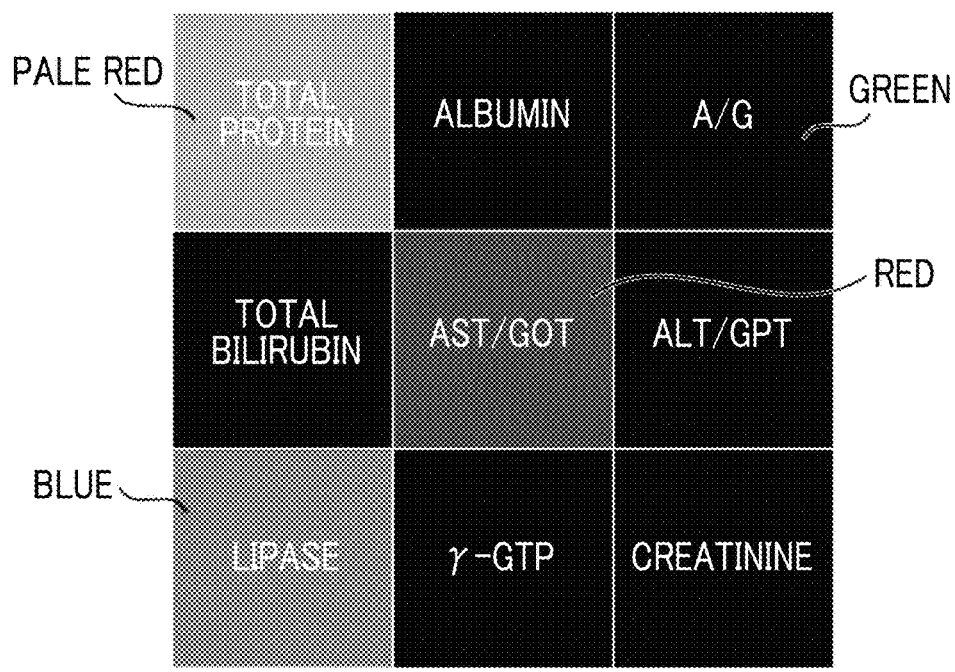
FIG. 9 is a diagram showing an example of a screen according to a modification example on which a plurality of inspection items are arranged and displayed in tiles.

In the embodiment, as an example, as shown in FIG. 9, a form may be made in which a plurality of inspection items are arranged and displayed on the display device 12 in tiles by changing color between the inspection items for which the last inspection result is an abnormal value and the inspection items for which the last inspection result is a normal value. In this case, a form may be made in which the inspection items for which the inspection result is an abnormal value are displayed on the display device 12 by further changing color depending on whether the inspection result is less than the lower limit value of the normal value or exceeds the upper limit value of the normal value. In this case, a form may be made in which the inspection items for which the inspection result is less than the lower limit value of the normal value are displayed on the display device 12 by changing density of color depending on a degree of difference from the lower limit value. In this case, a form may be made in which the inspection items for which the inspection result exceeds the upper limit value of the normal value are displayed on the display device 12 by changing density of color depending on a degree of difference from the upper limit value. A form in which the degree of difference in these cases is obtained in the same manner as the degree of abnormality is exemplified.

In the example of FIG. 9, the inspection items for which the inspection result is a normal value are displayed in green, the inspection items for which the inspection result exceeds the upper limit value of the normal value are displayed in red, and the inspection items for which the inspection result is less than the lower limit value of the normal value are displayed in blue. In the example of FIG. 9, when the degree of difference is higher, the display is performed with higher density of color.

A tile-shaped screen shown in FIG. 9 may be displayed in a free area of the first display screen and the second display screen or may be displayed as an initial screen. In a case where the tile-shaped screen is displayed as the initial screen, and in a case where an inspection item is designated on the tile-shaped screen, a faun in which a graph corresponding to the inspection item is displayed on the display device 12 is exemplified.

In the embodiment, a form may be made in which a scheduled date of a next medical examination is further displayed on at least one of the first display screen or the second display screen. The scheduled date in this case can be obtained, for example, by adding an interval (for example, once half a year) of a medical examination determined in advance for each variety and age to an execution date of a last medical examination.

In the embodiment, a form may be made in which, in a case where the print button is designated, an explanation of an inspection content of an inspection item, for which the inspection result is an abnormal value, and a method (for example, medication, exercise, food, or the like) of improving the inspection result are further printed.

In the embodiment, a form may be made in which, in a case where a graph displayed in the display area 62 is selected and a non-display instruction (for example, a double-tap operation or the like) is input, the selected graph is made to be not displayed. A form may be made in which, in a case where an inspection item displayed in the display area 64 is selected and a display instruction is input, the graph of the selected inspection item is made to be displayed in the display area 62.

In the embodiment, although a case where, for each of the inspection items for which the inspection result is determined to be an abnormal value by the determination unit 44, the graph representing the history of the inspection results and information representing a plurality of inspection results along the direction of the first axis are displayed has been described, the present disclosure is not limited thereto. For example, a form may be made in which, for each of all inspection items, the graph representing the history of the inspection results and information representing a plurality of inspection results along the direction of the first axis are displayed. For example, a form may be made in which, for an inspection item received by the reception unit 40 through a user's selection operation among the inspection items displayed in the display area 64, the graph representing the history of the inspection results and information representing a plurality of inspection results along the direction of the first axis are displayed.

In the embodiment, although a case where information representing a plurality of inspection results of the subject individual is displayed along the direction of the first axis has been described, the present disclosure is not limited thereto. For example, a form may be made in which information representing a plurality of inspection results of the same variety as the variety of the subject individual is displayed along the direction of the first axis. In this case, the examiner can ascertain the tendency of the inspection result of the same variety as the variety of the subject individual, instead of the subject individual. In this case, a form in which, as the inspection results used for display of information representing the plurality of inspection results, all inspection results of the same variety as the variety of the subject individual to be acquired from the inspection result table 16 storing the inspection results of the same variety or a part (for example, for last one year) of last inspection results are applied is exemplified. In addition, information representing a plurality of inspection results of the subject individual and information representing a plurality of inspection results of the same variety as the variety of the subject individual may be switched and displayed according to a user's operation.

Figure 10:
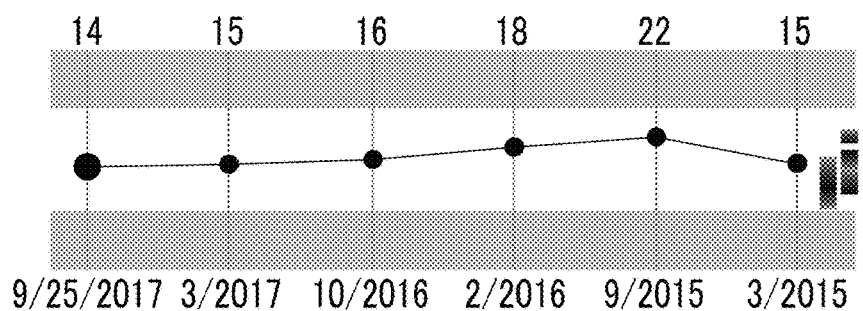
FIG. 10 is an enlarged view in which a part of a display screen according to a modification example is enlarged.

For example, as shown in FIG. 10, a form may be made in which both of information representing a plurality of inspection results of the subject individual and information representing a plurality of inspection results of the same variety as the variety of the subject individual are displayed along the direction of the first axis. In FIG. 10, an example where information representing a plurality of inspection results of the subject individual and information representing a plurality of inspection results of the same variety as the variety of the subject individual are arranged and displayed laterally is shown. For example, information representing a plurality of inspection results of the subject individual and information representing a plurality of inspection results of the same variety as the variety of the subject individual may be displayed by changing color. For example, information representing a plurality of inspection results of the subject individual may be displayed on a left side of the graph in a front view, and information representing a plurality of inspection results of the same variety as the variety of the subject individual may be displayed on a right side of the graph in a front view. In FIG. 10, a state in which one inspection item among the inspection items in the display area 62 shown in FIG. 5 is enlarged is shown. The state is the same as in FIGS. 11 to 18 described below.

Figure 11:
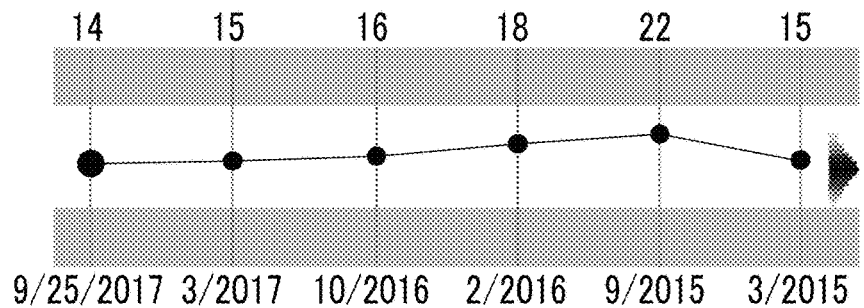
FIG. 11 is an enlarged view in which a part of a display screen according to a modification example is enlarged.
Figure 12:
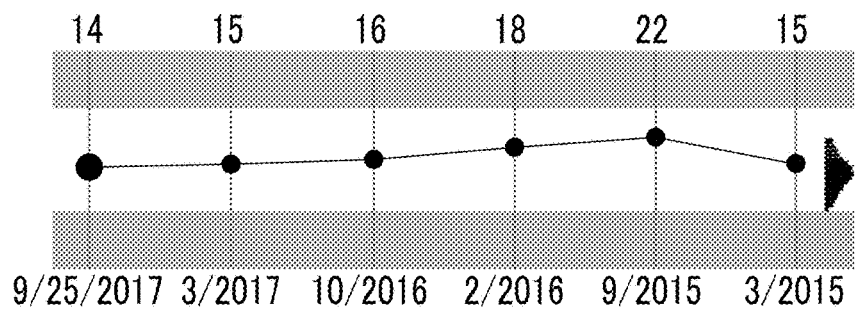
FIG. 12 is an enlarged view in which a part of a display screen according to a modification example is enlarged.

In the embodiment, as shown in FIG. 11, a form may be made in which information representing a plurality of inspection results is displayed along the direction of the first axis by a histogram. In FIG. 11, an example where, when a frequency is higher, density is higher, and rectangular points are extended in the direction of the second axis (a lateral direction of the screen in a front view) is shown. For example, as shown in FIG. 12, a form may be made in which information representing a plurality of inspection results is displayed along the direction of the first axis by a histogram of the same color and density.

Figure 13:
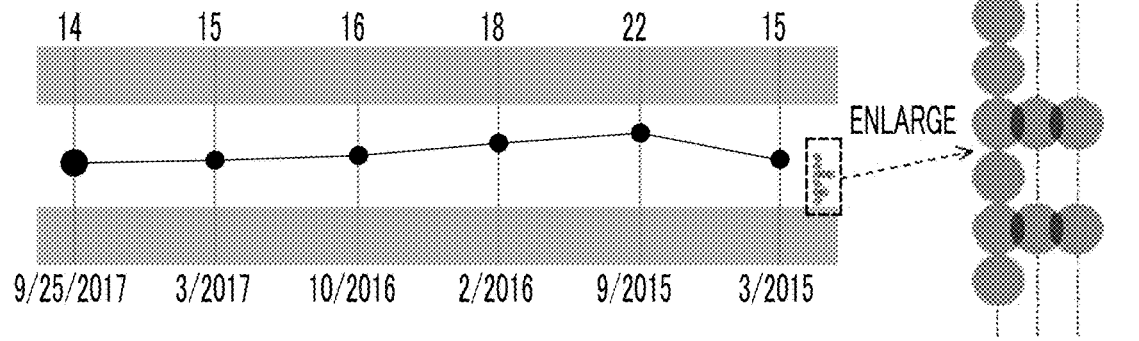
FIG. 13 is an enlarged view in which a part of a display screen according to a modification example is enlarged.

In the embodiment, although a case where information representing a plurality of inspection results is displayed on a position corresponding to one point of time of the second axis along the direction of the first axis has been described, the present disclosure is not limited thereto. For example, as shown in FIG. 13, a form may be made in which, in a case where a plurality of inspection results having the same value are present, information representing the inspection results having the same value is displayed on positions corresponding to different points of time of the second axis along the direction of the first axis. In FIG. 13, an example where a shape of a point representing one inspection result is a circular shape, and the number of positions (that is, the number of axes) corresponding to a point of time is three is shown. In this case, as shown in FIG. 13, in displaying information representing the inspection results having the same value by one point on each of different axes, a form in which points are displayed to partially overlap each other is exemplified. In this case, the overlapped portion is displayed with high density.

Figure 14:
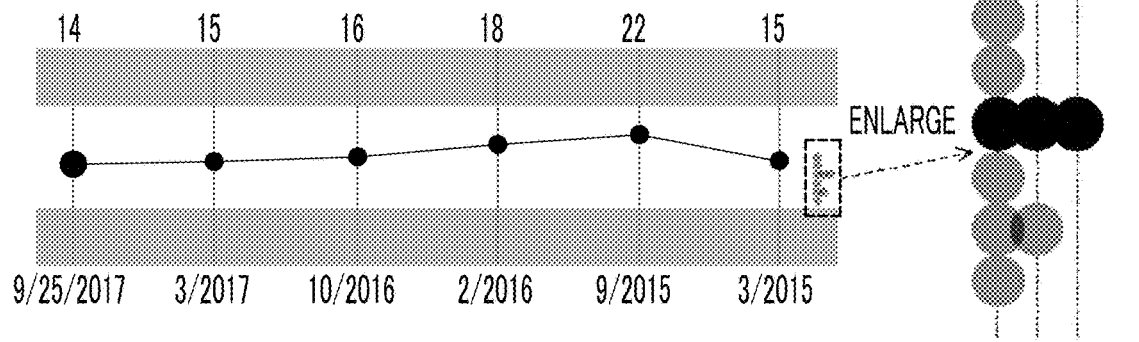
FIG. 14 is an enlarged view in which a part of a display screen according to a modification example is enlarged.

In this form example, as shown in FIG. 14, a form may be made in which an inspection result, the frequency of which exceeds the number of axes, is displayed with color different from an inspection result, the frequency of which is equal to or less than the number of axes. In FIG. 14, an example where the color of an inspection result, the frequency of which exceeds four, is different is shown.

Figure 15:
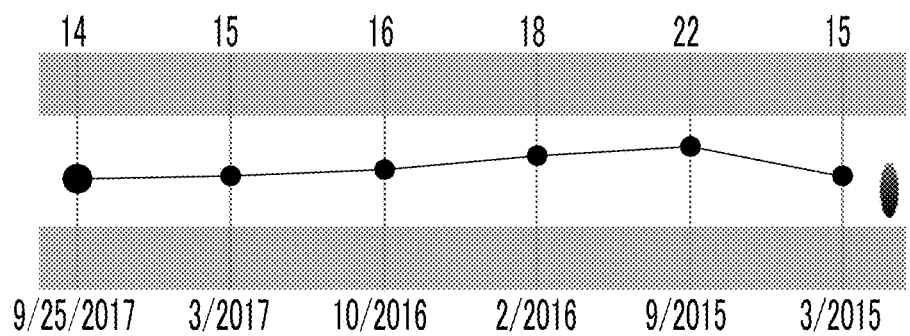
FIG. 15 is an enlarged view in which a part of a display screen according to a modification example is enlarged.
Figure 16:
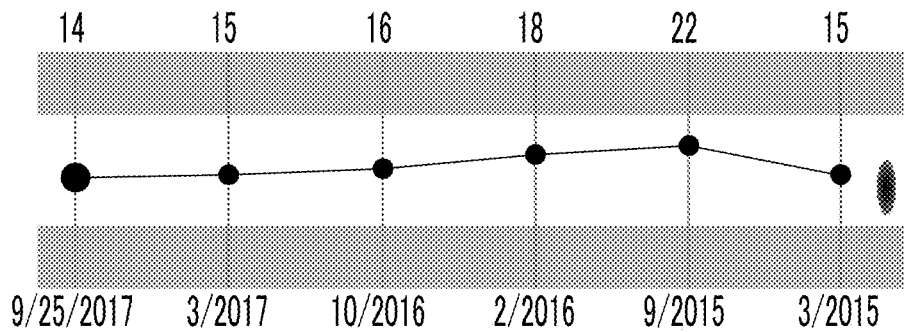
FIG. 16 is an enlarged view in which a part of a display screen according to a modification example is enlarged.

In the embodiment, although a case where a rectangular shape is applied as the shape of information representing a plurality of inspection results displayed along the direction of the first axis has been described, the present disclosure is not limited thereto. For example, as shown in FIG. 15, a forth may be made in which an elliptical shape is applied as the shape of information representing a plurality of inspection results. In the form example, as shown in FIG. 16, the density may be lowered with increase of the distance from the center along the direction of the second axis.

In the embodiment, the frequency of the inspection result may be weighted using a smaller weight value when the inspection result is older. In this case, a form in which 1 is used as the weight value of the inspection results for last three years (that is, a single inspection result becomes a frequency of 1), 0.5 is used as the weight value of the inspection results from last three years ago and until last six years (that is, two times of inspection results become a frequency of 1), and 0.25 is used as the weight value of the inspection results before last six years (that is, four times of inspection results become a frequency of 1) is exemplified.

Figure 17:
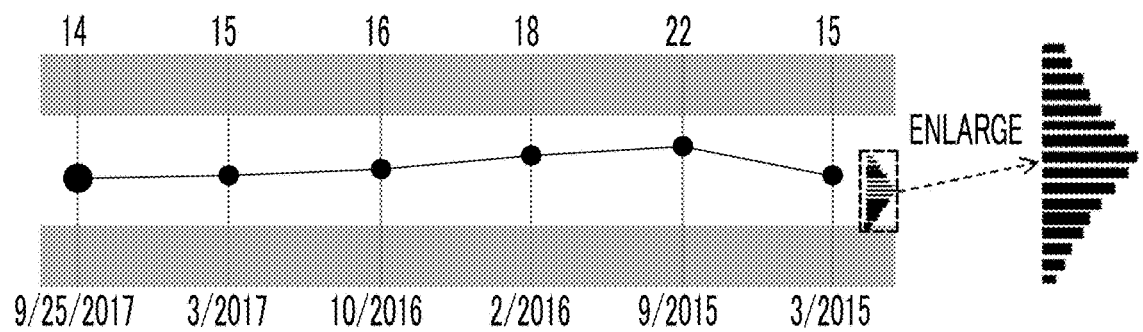
FIG. 17 is an enlarged view in which a part of a display screen according to a modification example is enlarged.

In the embodiment, a display state of information representing a plurality of inspection results displayed along the direction of the first axis may be changed depending on at least one the number of inspection results displayed along the direction of the first axis or the proportion of the inspection results before a predetermined point of time in the number of inspection results. Specifically, for example, in a case where the number of inspection result is equal to or less than a threshold value, information representing a plurality of inspection results is displayed along the direction of the first axis with color different from a case where the number of inspection result is equal to or greater than the threshold value. For example, in a case where the proportion of the inspection results before the predetermined point of time in the number of a plurality of inspection results is equal to or less than a threshold value, information representing a plurality of inspection results is displayed along the direction of the first axis with color different from a case where the proportion of the inspection results before the predetermined point of time in the number of a plurality of inspection results is equal to or greater than a threshold value. For example, as shown in FIG. 17, in a case where the number of inspection results displayed along the direction of the first axis is equal to or less than the threshold value, a histogram is displayed in a discrete manner. In these form examples, it is possible to ascertain the accuracy of the frequency of the inspection result based on at least one of the number of inspection results or the oldness of the inspection result.

Figure 18:
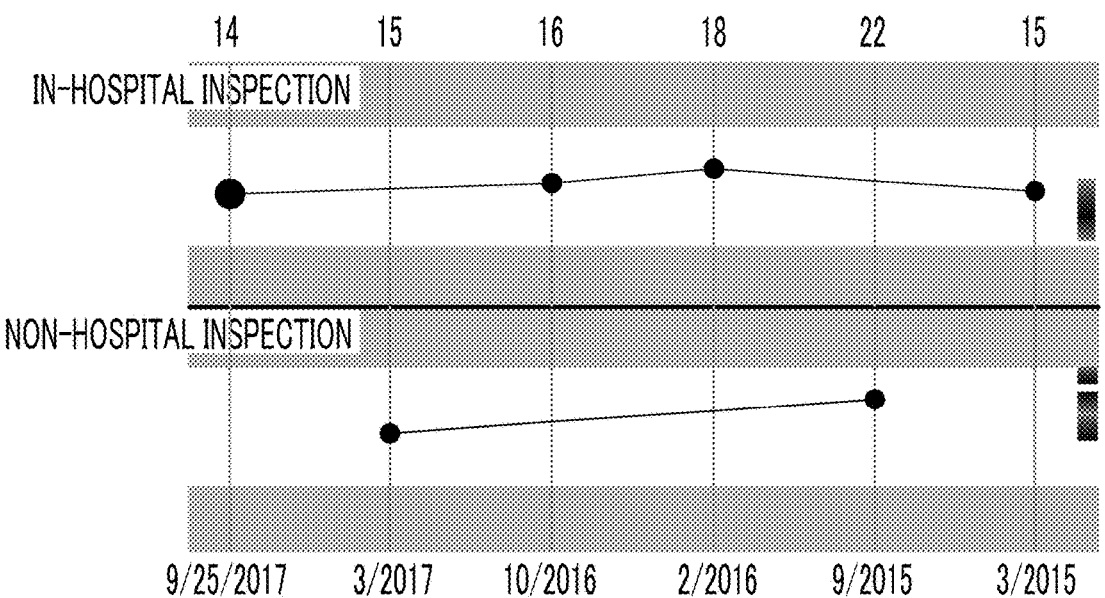
FIG. 18 is a diagram showing an example of a graph representing a history of inspection results according to a modification example.

In the embodiment, in regard to the graph displayed in the display area 62, an inspection result may be displayed to be distinguishable whether the inspection result is a result obtained by an in-hospital inspection or a result obtained by a non-hospital inspection can be distinguished. In this case, as shown in FIG. 18, a form in which a graph representing a history of inspection results obtained by the in-hospital inspection and a graph representing a history of inspection results obtained by the non-hospital inspection are arranged and displayed longitudinally is exemplified. In this case, for example, as shown in FIG. 18, information representing a plurality of inspection results displayed along the direction of the first axis may be divided and displayed into the in-hospital inspection and the non-hospital inspection. For example, in the graph of the display area 62 shown in FIG. 5, the inspection result obtained by the in-hospital inspection and the inspection result obtained by the non-hospital inspection may be displayed to be distinguishable by changing the color of the point to be plotted. The in-hospital inspection used herein means an inspection that is performed by inspection equipment provided in an animal hospital, and the non-hospital inspection means an inspection that is performed in a facility other than an animal hospital. In this case, a form in which information representing whether the inspection result is an inspection result obtained by the in-hospital inspection or an inspection result obtained by the non-hospital inspection is further stored in the inspection result information of the inspection result table 16 is exemplified.

In the embodiment, although a case where an animal other than a human is applied as the subject has been described, the present disclosure is not limited thereto. A form may be made in which a human is applied as the subject. In this case, the variety in the embodiment corresponds to a human race. In this case, a form may be made in which information representing a plurality of inspection results of the same age as the age of the subject may is displayed along the direction of the first axis with different color or density depending on the frequency of each inspection result. In this case, a form may be made in which information representing a predetermined number of inspection results of a relative of the subject is displayed along the direction of the first axis with different color or density depending on the frequency of each inspection result.

Various kinds of processing executed by the CPU executing software (program) in the embodiment may be executed by various processors other than the CPU. As the processor in this case, a programmable logic device (PLD) that is capable of changing a circuit configuration after manufacturing, such as a field-programmable gate array (FPGA), a dedicated electric circuit that is a processor having a circuit configuration designed dedicatedly to execute specific processing, such as an application specific integrated circuit (ASIC), or the like is exemplified. Various kinds of processing described above may be executed by one of various processors or may be executed by a combination of two or more processors of the same type or different types (for example, a combination of a plurality of FPGAs, a combination of the CPU and the FPGA, or the like). A hardware structure of each of various processors is more specifically an electric circuit in which circuit elements, such as semiconductor elements, are combined.

In the embodiment, although an aspect where the display control program 30 is stored (installed) in the storage unit 22 in advance has been described, the present disclosure is not limited thereto. The display control program 30 may be provided in a form of being recorded in a recording medium, such as a compact disk read only memory (CD-ROM), a digital versatile disk read only memory (DVD-ROM), or a universal serial bus (USB) memory. The display control program 30 may be in a form of being downloaded from an external device through a network.

What is claimed is:
1. A display control device comprising:
a processor that
displays a graph representing a history of inspection results including a last inspection result of a subject individual and a predetermined number of previous inspection results from the last inspection result for a predetermined inspection item among a plurality of inspection items in the subject, the graph having a first axis representing the inspection results and a second axis representing a time series, performs control for displaying information representing a plurality of inspection results of at least one of the subject individual or the same variety as a variety of the subject individual on a position corresponding to a specific point of time of the second axis along a direction of the first axis with a different color or density according to a frequency of each inspection result at the specific point of time, wherein a first frequency corresponds to a first color or a first density, and a second frequency corresponds to a second color or a second density, wherein the first frequency, the first color, and the first density are respectively different from the second frequency, the second color, and the second density, and performs control for displaying the inspection results in a diagram, wherein the diagram comprises a plurality of sub-axes, wherein in response to the frequency of each inspection result at the specific time not exceeding the number of the sub-axes, the processor displays each inspection result at the specific time respectively to a different sub-axis among the sub-axes, and wherein in response to the frequency of each inspection result at the specific time exceeding the number of the sub-axes, the processor displays each inspection result at the specific time respectively to all the sub-axes in an overlapping manner.

2. The display control device according to claim 1, wherein, in a case where the subject is an animal, the variety is an animal variety, and in a case where the subject is a human, the variety is a human race.

3. The display control device according to claim 1, wherein, in a case of performing control for displaying information representing the plurality of inspection results of the subject individual, the processor performs control for displaying information representing a plurality of previous inspection results before the predetermined number of inspection results of the subject individual.

4. The display control device according to claim 1, wherein, in a case of performing control for displaying information representing the plurality of inspection results of the same variety as the variety of the subject individual, the processor performs control for displaying information representing all inspection results to be acquired from a storage device storing the inspection results of the same variety or a part of last inspection results among all the inspection results.

5. The display control device according to claim 3, wherein the processor performs control for displaying information representing the plurality of inspection results of both of the subject individual and the same variety as the variety of the subject individual.

6. The display control device according to claim 1, wherein information representing the plurality of inspection results is a scatter plot on one axis in which a point corresponding to each of the plurality of inspection results is plotted on the position corresponding to the specific point of time.

7. The display control device according to claim 6, wherein, in a case where a plurality of inspection results having the same value are present, the processor performs control for displaying each piece of information representing the inspection results having the same value on a position corresponding to a different point of time along the direction of the first axis.

8. The display control device according to claim 1, wherein the processor performs control for displaying information representing the plurality of inspection results by a histogram.

9. The display control device according to claim 1, wherein the processor performs the control by weighting a frequency of an inspection result using a smaller weight value when the inspection result is older.

10. The display control device according to claim 1, wherein the processor performs control for displaying information representing the plurality of inspection results by changing a display state depending on at least one of the number of the plurality of inspection results or a proportion of inspection results before a predetermined point of time in the plurality of inspection results.

11. The display control device according to claim 10, wherein the processor performs control for displaying info, nation representing the plurality of inspection results by changing color depending on at least one of the number of the plurality of inspection results or the proportion of the inspection results before the predetermined point of time in the plurality of inspection results.

12. The display control device according to claim 1, wherein the processor further determines whether or not an inspection result is an abnormal value for each inspection item, wherein the predetermined inspection item is an inspection item for which an inspection result is determined to be an abnormal value.

13. The display control device according to claim 12, wherein the processor performs control for displaying the graph preferentially for the inspection item, for which the inspection result is determined to be the abnormal value, when a degree of abnormality is higher.

14. The display control device according to claim 1, wherein the processor further performs control for displaying a plurality of inspection items by changing color between an inspection item, for which an inspection result is an abnormal value, and an inspection item, for which an inspection result is a normal value.

15. The display control device according to claim 14, wherein the processor performs control for displaying the inspection item, for which the inspection result is the abnormal value, by further changing color depending on whether the inspection result is less than a lower limit value of the normal value or exceeds an upper limit value of the normal value.

16. The display control device according to claim 15, wherein the processor performs control for displaying an inspection item, for which an inspection result is less than the lower limit value of the normal value, by changing density of color depending on a degree of difference from the lower limit value, and performs control for displaying an inspection item, for which an inspection result exceeds the upper limit value of the normal value, by changing density of color depending on a degree of difference from the upper limit value.

17. The display control device according to claim 14, wherein the processor performs control for arranging and displaying the plurality of inspection items in tiles.

18. The display control device according to claim 1, wherein the processor performs control for switching between a first display screen, on which the graph is displayed in a medical examination of the subject, and a second display screen, on which the graph is displayed in a temporary inspection including inspection items different from inspection items in the medical examination.

19. The display control device according to claim 18, wherein the number of previous inspection results to be displayed as the graph on the first display screen is greater than the number of previous inspection results to be displayed as the graph on the second display screen.

20. The display control device according to claim 18, wherein the processor performs control for displaying the graph including inspection results of the medical examination as the history of the inspection results for the inspection items included in the medical examination among the inspection items in the temporary inspection.

21. A display control method executed by a computer, the method comprising:
    displaying a graph representing a history of inspection results including a last inspection result of a subject individual and a predetermined number of previous inspection results from the last inspection result for a predetermined lined inspection item among a plurality of inspection items in the subject, the graph having a first axis representing the inspection results and a second axis representing a time series,
    displaying information representing a plurality of inspection results of at least one of the subject individual or the same variety as a variety of the subject individual on a position corresponding to a specific point of time of the second axis along a direction of the first axis with a different color or density according to a frequency of each inspection result at the specific point of time, wherein a first frequency corresponds to a first color or a first density, and a second frequency corresponds to a second color or a second density, wherein the first frequency, the first color, and the first density are respectively different from the second frequency, the second color, and the second density, and
    performing control for displaying the inspection results in a diagram,
    wherein the diagram comprises a plurality of sub-axes,
    wherein in response to the frequency of each inspection result at the specific time not exceeding the number of the sub-axes, the processor displays each inspection result at the specific time respectively to a different sub-axis among the sub-axes, and
    wherein in response to the frequency of each inspection result at the specific time exceeding the number of the sub-axes, the processor displays each inspection result at the specific time respectively to all the sub-axes in an overlapping manner.

22. A non-transitory storage medium storing a program that causes a computer to execute a display control processing, the display control processing comprising:
    displaying a graph representing a history of inspection results including a last inspection result of a subject individual and a predetermined number of previous inspection results from the last inspection result for a predetermined inspection item among a plurality of inspection items in the subject, the graph having a first axis representing the inspection results and a second axis representing a time series,
    displaying information representing a plurality of inspection results of at least one of the subject individual or the same variety as a variety of the subject individual on a position corresponding to a specific point of time of the second axis along a direction of the first axis with a different color or density according to a frequency of each inspection result at the specific point of time, wherein a first frequency corresponds to a first color or a first density, and a second frequency corresponds to a second color or a second density, wherein the first frequency, the first color, and the first density are respectively different from the second frequency, the second color, and the second density, and
    performing control for displaying the inspection results in a diagram,
    wherein the diagram comprises a plurality of sub-axes,
    wherein in response to the frequency of each inspection result at the specific time not exceeding the number of the sub-axes, the processor displays each inspection result at the specific time respectively to a different sub-axis among the sub-axes, and wherein in response to the frequency of each inspection result at the specific time exceeding the number of the sub-axes, the processor displays each inspection result at the specific time respectively to all the sub-axes in an overlapping manner.

\* \* \* \* \*